US008097265B2

(12) United States Patent
Biering et al.

(10) Patent No.: US 8,097,265 B2
(45) Date of Patent: Jan. 17, 2012

(54) FOAM DISINFECTANT

(75) Inventors: Holger Biering, Grevenbroich (DE); Michael Decker, Solingen (DE)

(73) Assignee: Ecolab USA Inc., St. Paul, MN (US)

( * ) Notice: Subject to any disclaimer, the term of this patent is extended or adjusted under 35 U.S.C. 154(b) by 1753 days.

(21) Appl. No.: 10/518,784

(22) PCT Filed: Jun. 20, 2003

(86) PCT No.: PCT/EP03/06498

§ 371 (c)(1),
(2), (4) Date: Mar. 9, 2005

(87) PCT Pub. No.: WO2004/003126

PCT Pub. Date: Jan. 8, 2004

(65) Prior Publication Data

US 2010/0111877 A1 May 6, 2010

(30) Foreign Application Priority Data

Jun. 27, 2002 (DE) .................................. 102 28 656

(51) Int. Cl.

| | |
|---|---|
| ***A01N 25/00*** | (2006.01) |
| ***A61K 31/205*** | (2006.01) |
| ***A61K 31/13*** | (2006.01) |
| *A01N 37/30* | (2006.01) |
| *A01N 33/00* | (2006.01) |

(52) U.S. Cl. ........ 424/405; 514/554; 514/556; 514/579; 514/945

(58) Field of Classification Search ........................ None
See application file for complete search history.

(56) References Cited

U.S. PATENT DOCUMENTS

| | | | | |
|---|---|---|---|---|
| 5,403,505 | A | 4/1995 | Hachmann et al. | |
| 5,635,469 | A * | 6/1997 | Fowler et al. | 510/406 |
| 5,646,105 | A | 7/1997 | Hachmann et al. | |
| 5,856,290 | A | 1/1999 | Van Buskirk et al. | |
| 5,951,993 | A * | 9/1999 | Scholz et al. | 424/405 |
| 6,140,289 | A | 10/2000 | McCandlish et al. | |
| 6,323,171 | B1 | 11/2001 | Fonsny et al. | |
| 2004/0200725 | A1 * | 10/2004 | Yahalom et al. | 205/98 |

FOREIGN PATENT DOCUMENTS

| | | |
|---|---|---|
| DE | 2001317 | 1/1970 |
| DE | 19615286 | 10/1997 |
| EP | 0333143 | 3/1989 |
| WO | WO 95/00613 | 1/1995 |
| WO | WO 98/27188 | 6/1998 |
| WO | WO 99/31216 | 6/1999 |

OTHER PUBLICATIONS

Birdi (Surface and colloid chemistry: principles and applications; 2009, CRC Press; p. 169).*
Edited by Kenneth J. Lissant, Emulsion and Emulsion Technology Part 1, p. 115, 1974.

* cited by examiner

*Primary Examiner* — Ernst Arnold
(74) *Attorney, Agent, or Firm* — Merchant & Gould P.C.

(57) ABSTRACT

The invention relates to an aqueous foam disinfectant comprised of a special surfactant system, which consists of nonionic and amphoteric surfactants, and of a synergistic disinfectant constituent, which consists of an antimicrobial agent having amino groups and of at least one additional antimicrobial agent.

11 Claims, No Drawings

FOAM DISINFECTANT

This application is a national stage entry of and claims priority to PCT/EP03/06498, filed on Jun. 20, 2003, that claims priority to German application number 10228656.6, filed on Jun. 27, 2002.

This invention relates to water-based foam disinfectants containing a surfactant system of nonionic and amphoteric surfactants capable of generating foam and a synergistic disinfectant combination. The present invention also relates to a process for the foam disinfection of surfaces using a foam generating unit and to the use of the foam disinfectants according to the invention for disinfecting surfaces.

The use of compositions applied to surfaces in the form of a foam has already been described in various documents. One example of this is German patent application DE 20 01 317.

In most of the known cases, the corresponding formulations contain anionic surfactants such as, for example, sodium lauryl sulfate, sodium dodecyl benzenesulfonate, sodium salts of lauryl sarcosinate and, in some cases, surfactants which further improve the stability of the foam such as, for example, lauryl diethanolamide. The main advantage of foaming formulations is that they can be used much more effectively than other formulations for cleaning and disinfecting surfaces. This is due above all to the better wetting of the surfaces, particularly non-horizontal surfaces. By virtue of this better wetting, the formulations adhere to the surface for a longer time with the result that the disinfecting effect is increased through the longer contact time. Another advantage of foaming formulations is that, when they are sprayed, they form droplets of such a size that there is no relevant risk of exposure through inhalation. This is particularly important where microbicides or other formulation ingredients with potentially irritating or caustic properties are used. However, the surfactant systems normally used are not equally effective in all formulations. In particular, in cases where formulations containing aminic or cationic biocides are to be produced, anionic surfactants are not appropriate on account of possible precipitations.

On the one hand, the expert knows that long-chain fatty amines and salts thereof and aliphatic diamines are very effective microbicides with a broad action spectrum. On the other hand, it is also known in practice that the use of aminic biocides can lead to sensitization of the skin. This is reflected in reddening of the skin where it comes into contact with the amines.

In addition, the ecotoxicity of such amines is often a disadvantage. With excessive concentrations, the microflora of the particular sewage treatment plant can even be significantly affected. Accordingly, the problem addressed by the present invention was to formulate and use aminic microbicides in such a way that only small quantities would be necessary.

Accordingly, the present invention was mainly concerned with providing new combinations of surfactant systems capable of generating foam and aminic biocides in conjunction with other antimicrobial agents.

The present invention relates to foam disinfectants containing 0.1 to 10% by weight of a surfactant system of nonionic and amphoteric surfactants capable of generating foam in contact with amines and a synergistic disinfectant combination consisting of an antimicrobial agent containing amino groups and at least one other antimicrobial agent.

Foam disinfectants in the context of the invention are preferably foam disinfectants which contain nonionic surfactants selected from the groups of fatty alcohol ethoxylates and alkyl polyglycosides and amphoteric surfactants selected from the group of acetobetaines as their surfactant system.

In a particularly preferred embodiment, the surfactant system mentioned contains at least one surfactant from each of the groups of fatty alcohol ethoxylates, alkyl polyglycosides and acetobetaines.

In a preferred embodiment, the surfactant groups of fatty alcohol ethoxylates, alkyl polyglycosides and acetobetaines mentioned are present in a quantity by weight ratio to one another of (5 to 7):(2 to 4):(0.5 to 1.5).

With regard to the amine-containing microbicide, the foam disinfectant according to the invention preferably contains an antimicrobial agent with amino groups in a total quantity of 0.001 to 10% by weight, based on the disinfectant as a whole.

In a particularly advantageous embodiment, the amino-functional antimicrobial agent mentioned is selected from alkylamines corresponding to formula (e) (I) and/or (II):

$R^1$—NH—$(CH_2)_3NH_2$ (I), $R^1$—N—$[(CH_2)_3NH_2]_2$ (II), where $R^1$ is a $C_{8-18}$ and preferably $C_{12-14}$ alkyl group, which may be present in unneutralized or partly or completely neutralized form, and/or active substances obtainable by reacting a propylenediamine corresponding to formula (I):

$R^1$—NH—$(CH_2)_3NH_2$ (I)

with a glutamic acid or glutamic acid derivatives corresponding to formula (III):

$R^2$—O—CO—$(CH_2)_2$—CH($NH_2$)—COOH (III)

where $R^2$ is hydrogen or a $C_{1-4}$ alkyl group, and optionally reacting the resulting product with ethylene oxide and/or propylene oxide, optionally followed by further reaction with organic or inorganic acids.

As mentioned at the beginning, amine-containing microbicides cannot be used without problems. To overcome disadvantages, the foam disinfectant according to the invention is combined with at least one other antimicrobial agent preferably selected from the group of low molecular weight alcohols corresponding to formula (IV):

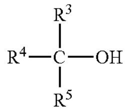

(IV)

where $R^3$, $R^4$ and $R^5$ independently of one another represent H atoms or alkyl groups containing 1 to 3 carbon atoms, the total number of carbon atoms being no greater than 6.

It is emphasized that the problem is solved particularly well if the foam disinfectant according to the invention contains an alcohol selected from ethanol, 1-propanol and 2-propanol or mixtures thereof, the total content of alcohols, based on the disinfectant as a whole, preferably being from 20 to 50% by weight and more preferably from 20 to 40% by weight. The required generation of foam and foam stability are particularly pronounced when ethanol and/or i-propanol is/are present in the foam disinfectant.

Besides or instead of the alcohol mentioned, the foam disinfectant according to the invention may of course also contain as antimicrobial agent another antimicrobial component selected from the groups of alcohols not covered by formula (IV), antimicrobial acids, carboxylic acid esters, acid amides, phenols, phenol derivatives, diphenyls, diphenyl alkanes, urea derivatives, oxygen, nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propynyl butyl carbamate, iodine and iodophores, undecylenic acid, citric acid, 2-benzyl-4-chlorophenol, 2,2'-methylene-bis-(6-bromo-4-chlorophenol), 2,4,4'-trichloro-2'-hydroxydiphenylether, N-(4-chlorophenyl)-N-(3,4-dichlorophenyl)-urea, N,N'-(1,10-decanediyldi-1-pyridinyl-4-ylidene)-bis-(1-octaneamine)-dihydrochloride, N,N'-bis-(4-chlorophenyl)-3,12-diimino-2,4,11,13-tetraazatetradecane diimidoamide, quaternary ammonium compounds, guanidines and amphoterics being particularly suitable.

Particular emphasis is placed in this respect on quaternary ammonium compounds, as can also be seen in the Examples (E1).

The foam disinfectant according to the invention preferably contains, based on the disinfectant as a whole, 0.005 to 2.0% by weight of the above-mentioned antimicrobial agent containing amino groups, 20 to 40% by weight of the above-mentioned alcohols (IV) or mixtures thereof, 0.5 to 5% by weight of the above-mentioned surfactant system, 0 to 6% by weight of typical additives, such as complexing agents and perfume, and optionally water and/or other typical auxiliaries and additives as the balance to 100% by weight.

The present invention also relates to a process for the foam disinfection of surfaces in which a foam disinfectant according to the invention is applied to the above-mentioned surfaces in the form of a foam by means of a foam-generating unit, for example a foam spray bottle, the foam optionally being removed after a sufficient contact time by rinsing with water or wiping with a cloth.

The present invention also relates to the use of the foam disinfectant according to the invention for disinfecting surfaces.

The use according to the invention has proved to be particularly effective in the disinfection of surfaces in the medical field, in the food-manufacturing and/or processing industry, in hotels, in public buildings and institutions.

In the testing of the disinfectants according to the invention, it was found to be an advantage that the formulations according to the invention form a stable foam in use despite their high alcohol content and still show adequate antimicrobial activity. In addition, the surfaces dry in a very short time after application of the formulations.

EXAMPLES

1. Preparation of Test Solutions

Test solutions E1 to E3 according to the invention and comparison solutions V1 to V4 (Table 1) were prepared simply by combining various individual constituents, preferably with stirring.

TABLE 1

| | Test solutions | | | | | | |
|---|---|---|---|---|---|---|---|
| Individual constituents (% by wt.) (based on the solution as a whole) | E1 | E2 | E3 | V1 | V2 | V3 | V4 |
| Alkyl-($C_{8-14}$)-polyglucoside (Glucopon ® 650) | 0.75 | 0.75 | 0.5 | — | 1.6 | — | — |
| Dimethyl-$C_{8-18}$-acylamidopropyl acetobetaine (Dehyton ® K) | 0.25 | 0.25 | 0.2 | — | — | — | 1.6 |
| Isotridecyl fatty alcohol ethoxylate (8 EO) (Lutensol ® TO 89) | 1.5 | 1.5 | 0.9 | — | — | 1.6 | — |
| Dimethylalkyl-($C_{12-14}$)-benzylammonium chloride | — | 0.15 | — | — | — | — | — |
| Glucoprotamin ® | — | 0.05 | — | — | — | — | — |
| Lauryl dipropylenetriamine | — | — | 0.3 | 0.3 | 0.3 | 0.3 | 0.3 |
| Ethanol (96% by volume) | 5.0 | 5.0 | — | — | — | 40.0 | — |
| 2-Propanol | 25.0 | 25.0 | 30.0 | 40.0 | 30.0 | — | — |
| 1-Propanol | — | — | | — | — | — | 40.0 |
| Water | | | | | | | |

2. Testing of the Activity of Examples E1 and E2 According to the Invention Against the Gram-Positive Bacterium *Staphylococcus aureus*

Bactericidal activity was tested against the test germ *Staphylococcus aureus* by the quantitative suspension test according to the Richtlinien der Deutschen Gesellschaft für Hygiene and Mikrobiologie using undiluted mixtures E1 and E2. The results are set out in Table 2. It can be seen that the mixtures mentioned have an excellent effect in some cases after only 0.5 mins. (E2) and particularly after 3 mins.

TABLE 2

Effectiveness of Examples E1 and E2 according to the invention against the gram-positive bacterium *Staphylococcus aureus*

| | Germ reduction (log stages) | | |
|---|---|---|---|
| Test preparation | 0.5 mins | 1 min. | 3 mins. |
| Mixture E1 | <1.10 | 1.98 | 4.82 |
| Mixture E2 | >5.49 | >5.41 | >5.38 |

3. Testing of the Drying Behavior of Examples E1 and E2 According to the Invention In order to determine drying behavior on surfaces, 0.3 g of mixtures E1 and E2 was applied to 100 $cm^2$ ceramic tiles using a foam spray and the time taken by the surface to visibly dry was determined. The results are set out in Table 3.

TABLE 3

| Drying behavior of Examples E1 and E2 according to the invention | |
|---|---|
| Test preparation | Drying time (mins.) |
| Mixture E1 | 2.0 |
| Mixture E2 | 2.5 |

4. Testing of the Foaming Behavior of Examples E1 to E3 by Comparison with Reference Solutions V1 to V4

In order to test foaming behavior, mixtures E1 to E3 and V1 to V4 were applied to a PVC surface by means of a grid foam spray. For optimal use, a vigorous foam that collapses 1 to 2 minutes after application to the surface should be formed from a clear solution during spraying. The results are set out in Table 4. It can clearly be seen that combinations E1 to E3 according to the invention have advantages over comparison formulations V1 to v4 in regard to foaming behavior.

TABLE 4

Testing of the foaming behavior of E1 to E3 by comparison with V1 to V4.

| | Test parameter | | |
|---|---|---|---|
| Mixture | Appearance of the solution | Consistency of the foam | Stability of the foam |
| V1 | Clear, colorless | Thin foam | None |
| V2 | Cloudy, milky | Medium foam | Ca. 3.5 mins. |
| V3 | Clear, colorless | Vigorous foam | Ca. 30 secs. |
| V4 | Clear, colorless | Thin foam | Ca. 5 secs. |
| E1 | Minimal clouding, colorless | Vigorous foam | Ca. 90 secs. |
| E2 | Minimal clouding, colorless | Vigorous foam | Ca. 90 secs. |
| E3 | Clear, colorless | Vigorous foam | Ca. 90 secs. |

The invention claimed is:

1. A water-based foam disinfectant comprising:

a) about 0.1 to about 10% by weight of a surfactant system comprising:

(i) at least one nonionic surfactant; and (ii) at least one amphoteric surfactant, wherein the nonionic surfactant and amphoteric surfactant are capable of generating foam in the presence of an amine;

b) a first antimicrobial agent selected from the group consisting of (i) alkylamines having the formula $R^1—NH—(CH_2)_3NH_2$;

(ii) alkylamines having the formula $R^1—N—[(CH_2)_3NH_2]_2$; and (iii) a reaction product of a propylenediamine of formula $R^1—NH—(CH_2)_3NH_2$ with glutamic acid or glutamic acid derivatives of formula $R^2—O—CO—(CH_2)_2—CH(NH_2)—COOH$, wherein $R^1$ is a $C_{8-18}$ alkyl group and $R^2$ is hydrogen or a $C_1$-$C_4$ alkyl group, and c) about 20 to 50 wt.% of one or more low molecular weight alcohol having the formula

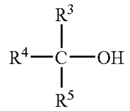

where $R^3$, $R^4$ and $R^5$ independently represent hydrogen atoms, or alkyl groups having 1 to 3 carbon atoms, the total number of carbon atoms being not greater than 6.

2. The composition of claim 1, wherein the nonionic surfactant is selected from the group consisting of fatty alcohol ethoxylates, alkyl polyglycosides, and mixtures thereof.

3. The composition of claim 1, wherein the amphoteric surfactant is an acetobetaine.

4. The composition of claim 1, wherein the composition contains at least one surfactant from each of the groups of fatty alcohol ethoxylate, alkyl polyglycoside, and acetobetaine.

5. The composition of claim 4, wherein the surfactant groups of fatty alcohol ethoxylate, alkyl polyglycoside, and acetobetaine are present in a quantity by weight ratio to one another of 5 to 7:2 to 4:0.5 to 1.5.

6. The composition of claim 1, wherein the first antimicrobial agent is present in the total quantity of 0.001 to 10% by weight, based on the disinfectant as a whole.

7. The composition of claim 1, wherein the alcohol is selected from the group consisting of ethanol, 1-propanol, and 2-propanol.

8. The composition of claim 1, wherein the reaction product is reacted with ethylene oxide or propylene oxide.

9. A water-based foam disinfectant comprising:

a) about 0.1 to about 10% by weight of a surfactant system comprising fatty alcohol ethoxylate, alkyl polyglycoside, and acetobetaine present in a quantity by weight ratio to one another of (5 to 7):(2 to 4):(0.5 to 1.5), capable of generating foam in the presence of an amine;

b) a first antimicrobial agent containing an amino group, and c) about 20 to 50 wt.% of one or more low molecular weight alcohol having the formula

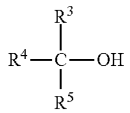

where $R^3$, $R^4$ and $R^5$ independently represent hydrogen atoms, or alkyl groups having 1 to 3 carbon atoms, the total number of carbon atoms being not greater than 6.

10. The composition of claim 9, wherein the first antimicrobial agent is present in the total quantity of 0.001 to 10% by weight, based on the disinfectant as a whole.

11. The composition of claim 9, wherein the alcohol is selected from the group consisting of ethanol, 1-propanol, and 2-propanol.

* * * * *